US00PP09793P

United States Patent [19]

VandenBerg

[11] Patent Number: Plant 9,793

[45] Date of Patent: Feb. 4, 1997

[54] CHRYSANTHEMUM PLANT NAMED 'HELEN'

[75] Inventor: Cornelis P. VandenBerg, Salinas, Calif.

[73] Assignee: Yoder Brothers, Inc., Barberton, Ohio

[21] Appl. No.: 608,622

[22] Filed: Mar. 1, 1996

[51] Int. Cl.[6] ..... A01H 5/00

[52] U.S. Cl. ..... Plt./82

[58] Field of Search ..... Plt./76, 82

[56] References Cited

U.S. PATENT DOCUMENTS

P.P. 8,982 11/1994 VandenBerg ..... Plt./82

*Primary Examiner*—Howard J. Locker
*Attorney, Agent, or Firm*—Foley & Lardner

[57] ABSTRACT

A Chrysanthemum plant named Helen particularly characterized by its flat capitulum form; decorative capitulum type; red ray floret color; diameter across face of capitulum of 41 to 51 mm when fully opened; branching pattern is spreading and prolific, with 6 to 8 laterals developing after pinch when grown outside under natural daylength in fall flowerings; natural season flower date of August 15 to 16 when planting rooted cuttings on June 17 to 18 in Salinas, Calif., and of September 19 to 22 when planting rooted cuttings June 15 to 18 in Hightstown, N.J.; plant height of 25 to 33 cm when grown in fall under natural daylength with no growth regulators; and durable, uniform performance.

3 Drawing Sheets

The present invention comprises a new and distinct cultivar of Chrysanthemum, botanically known as *Dendranthema grandiflora,* and referred to by the cultivar name Helen.

Helen, identified as 8090 (92-521005), was originated from a cross made by Cornelis P. VandenBerg in a controlled breeding program in Salinas, Calif., in November of 1991.

The female parent of Helen was the cultivar identified as Bravo, disclosed in U.S. Plant Pat. No. 6,888, and described as garden mum with red flower color.

The male parent of Helen was an unnamed seedling, identified as 8333 (89-765001), and described as a pink decorative garden mum with many disc florets. The male parent was discarded from all programs after completion of the breeding program, in 1991.

Helen was discovered and selected as one flowering plant within the progeny of the stated cross by Cornelis P. VandenBerg in October of 1992 in a controlled environment in Salinas, Calif.

The first act of asexual reproduction of Helen was accomplished when vegetative cuttings were taken from the initial selection in December of 1992 in a controlled environment in Salinas, Calif., by technicians working under the supervision of Cornelis P. VandenBerg.

Horticultural examination of controlled flowerings of successive plantings has shown that the unique combination of characteristics as herein disclosed for Helen are firmly fixed and are retained through successive generations of asexual reproduction.

Helen has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Helen, which, in combination, distinguish this Chrysanthemum as a new and distinct cultivar:

1. Flat capitulum form.
2. Decorative capitulum type.
3. Red ray floret color.
4. Diameter across face of capitulum of 41 to 51 mm when fully opened.
5. Branching pattern is spreading and prolific, with 6 to 8 laterals developing after pinch when grown outside under natural daylength in fall flowerings.
6. Natural season flower date of August 15 to 16 when planting rooted cuttings on June 17 to 18 in Salinas, Calif., and of September 19 to 22 when planting rooted cuttings June 15 to 18 in Hightstown, N.J.
7. Plant height of 25 to 33 cm when grown in fall under natural daylength with no growth regulators.
8. Durable, uniform performance.

The accompanying photographic drawings show typical inflorescence and leaf characteristics of Helen, with the colors being as nearly true as possible with illustrations of this type.

Sheet 1 is a color photograph of Helen grown in natural season outside conditions in Salinas, Calif.

Sheet 2 is a black and white photograph of three views of the inflorescence of Helen.

Sheet 3 is a black and white photograph showing the upper and under sides of the leaves of Helen at 3 stages of development (mature, intermediate and immature).

In sheets 2 and 3 a measuring tape in centimeters has been added.

Of the commercial cultivars known to the inventor, the most similar in comparison to Helen is the female parent Bravo. Reference is made to attached Chart A, which compares certain characteristics of Helen to the same characteristics of Bravo.

Similar traits are capitulum form and type, and branching pattern. The ray floret color of Helen (R.H.S. between 46A and 185A) is slightly darker than the ray floret color of Bravo (R.H.S. 46A). Helen has a larger diameter of capitulum, a faster natural season flowering response and a shorter plant height when compared with Bravo.

In the following description color references are made to The Royal Horticultural Society Colour Chart. The color values were determined on plant material grown as a pinched garden mum grown outdoors in Salinas, Calif. on Aug. 16, 1995.

Classification:

*Botanical.*—*Dendranthema grandiflora* cv Helen.

*Commercial.*—Flat decorative garden mum.

INFLORESCENCE

A. Capitulum:

*Form.*—Flat.

*Type.*—Decorative.

*Diameter across face.*—41 to 51 mm when fully opened.

B. Corolla of ray florets:

*Color (general tonality from a distance of three meters).*—Red.

*Color (upper surface)* .—Between 46A and 185A.

*Color (under surface).*—185B, streaked with 173D.

*Shape.*—Outer ray florets convex, longitudinal straight, ray floret tips rounded.

C. Corolla of disc florets:

*Color (mature).*—14B.

*Color (immature).*—14B, overlaid with 144B.

D. Reproductive organs:

*Androecium.*—Present on disc florets only; very few, scant to no pollen.

*Gynoecium.*—Present on both ray and disc florets.

PLANT

A. General appearance:

*Height.*—25 to 33 cm when grown in fall under natural daylength with no growth regulators.

*Branching pattern.*—Spreading and prolific.

B. Foliage:

*Color (upper surface).*—147A.

*Color (under surface).*—147B.

*Shape.*—Small, narrow, deeply lobed, slightly serrated.

CHART A

COMPARISONS MADE OF PLANTS GROWN UNDER NATURAL SEASON OUTDOOR CONDITIONS IN SALINAS, CALIFORNIA AND IN HIGHTSTOWN, NEW JERSEY

| CULTIVAR | HELEN | BRAVO |
|---|---|---|
| Ray floret color | Red | Red |
| Capitulum form and type | Flat decorative | Flat decorative |
| Diameter across face of capitulum | 41 to 51 mm | 38 to 47 mm |
| Branching pattern | Spreading | Spreading |
| Nat. season flower date: | | |
| in Salinas, CA | Aug 15 to 16 | Aug 16 to 23 |
| in Highstown, NJ | Sep 19 to 22 | Sep 24 to 27 |
| Plant height: | 25 to 33 cm | 30 to 35 cm |

What is claimed is:

1. A new and distinct Chrysanthemum plant named Helen, as described and illustrated.

* * * * *

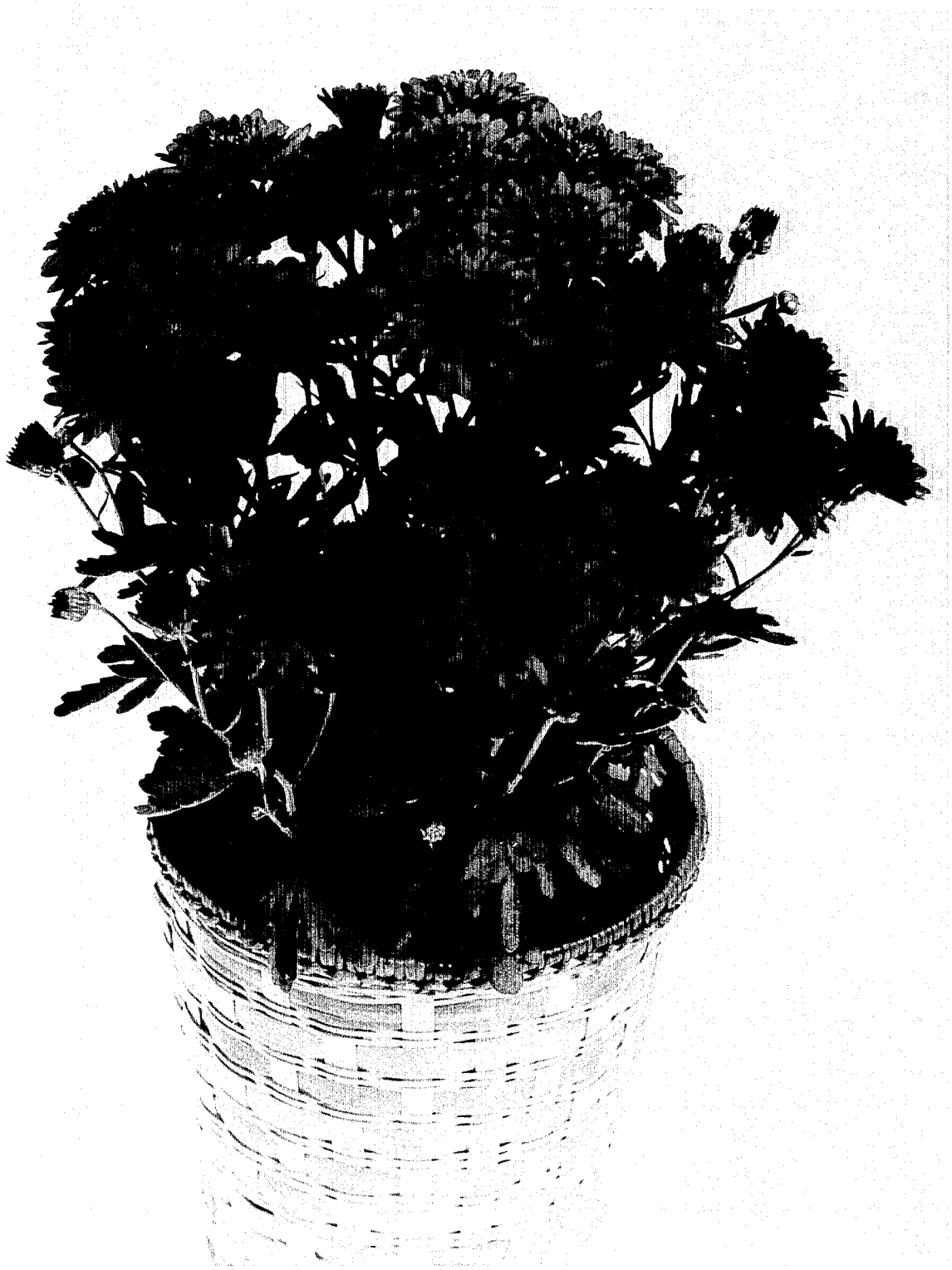

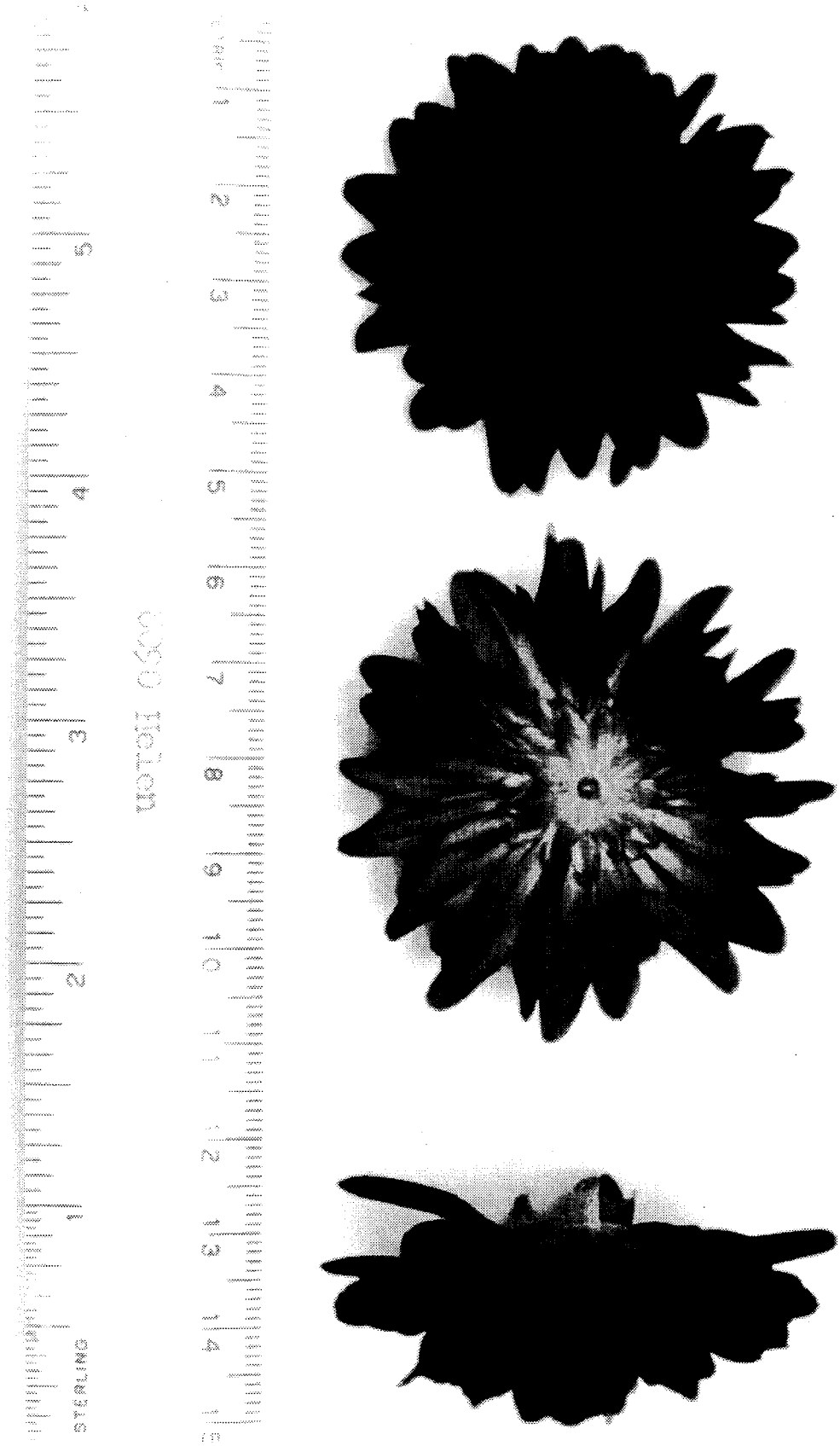
STERLING
COTOT 0600

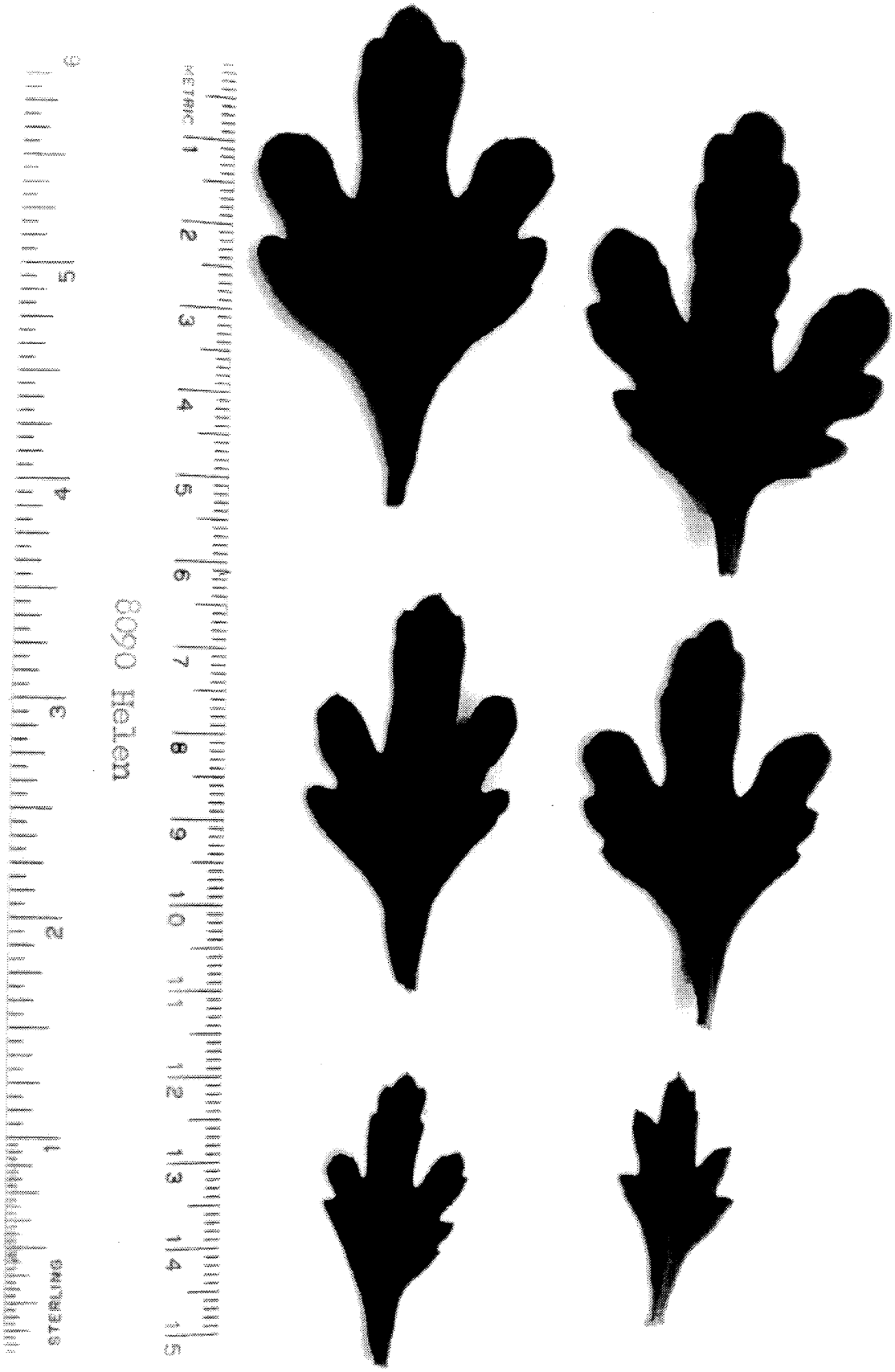
STERLING
METRIC
Helen 0608